(12) United States Patent (10) Patent No.: US 8,463,014 B2
Movassaghi et al. (45) Date of Patent: Jun. 11, 2013

(54) OPTIMAL ROTATIONAL TRAJECTORY DETERMINATION FOR RA BASED ON PRE-DETERMINED OPTIMAL VIEW MAP

(75) Inventors: Babak Movassaghi, Denver, CO (US); Onno Wink, Denver, CO (US); Shiuh-Yung James Chen, Englewood, CO (US); Joel Alberto Garcia, Denver, CO (US); John D. Carroll, Littleton, CO (US)

(73) Assignees: The Regents of the University of Colorado, a body corporate, Denver, CO (US); Koninklijke Philips Electronics N.V., Eindhoven (NL)

( * ) Notice: Subject to any disclaimer, the term of this patent is extended or adjusted under 35 U.S.C. 154(b) by 958 days.

(21) Appl. No.: 12/305,989

(22) PCT Filed: Jun. 18, 2007

(86) PCT No.: PCT/IB2007/052324
§ 371 (c)(1),
(2), (4) Date: Aug. 27, 2009

(87) PCT Pub. No.: WO2008/001260
PCT Pub. Date: Jan. 3, 2008

(65) Prior Publication Data
US 2010/0014740 A1 Jan. 21, 2010

(30) Foreign Application Priority Data
Jun. 28, 2006 (EP) ..................................... 06116183

(51) Int. Cl.
*G06K 9/00* (2006.01)
(52) U.S. Cl.
USPC ............................ 382/132; 382/128; 382/130

(58) Field of Classification Search
USPC .................................................. 382/128–132
See application file for complete search history.

(56) References Cited

U.S. PATENT DOCUMENTS

| 5,381,791 | A | * | 1/1995 | Qian | 600/436 |
| 6,501,848 | B1 | * | 12/2002 | Carroll et al. | 382/128 |
| 2010/0014740 | A1 | * | 1/2010 | Movassaghi et al. | 382/132 |

FOREIGN PATENT DOCUMENTS

| WO | WO2004012152 | 2/2004 |
| WO | WO2006018768 | 2/2006 |

OTHER PUBLICATIONS

"Computer Assisted Coronary Intervention by Use of On-line 3D Reconstruction and Optimal View Strategy", Chen S-Y J; Carroll J D, Medical Image Computing and Computer Assisted Intervention, p. 377-385, Oct. 11, 1998.*

(Continued)

*Primary Examiner* — Joseph Burgess

(57) ABSTRACT

A method for determining an optimal trajectory for 3-dimensional rotational X-ray coronary angiography for a C-arm X-ray system that has at least two degrees of freedom, where the C-arm X-ray system is defined by a rotational movement of the C-arm expressed in a left/right coronary artery oblique angle, and a roll motion of the C-arm expressed in a caudal/cranial angle. The method includes generating of a 3-dimensional representation of a center-line of a body vessel in a region of interest. generating at least one optimal view map. Further, an optimal trajectory for the X-ray system within the optimal view map is determined, where an optimal trajectory is at least determined by movements of the C-arm within its two degrees of freedom allowing image projections with minimal foreshortening and/or overlap while minimizing an exposure to X-rays.

14 Claims, 15 Drawing Sheets

OTHER PUBLICATIONS

Wink et al., "Coronary Intervention Planning Using Hybrid 3D Reconstruction", Medical Image Computing and Computer-Assisted Intervention—MICCAI 2002, 5th International Conference, Proceed, Part I, Lecture Notes in Computer Science, vol. 2488, Springer-Verlag, Berlin, Germany, 2002, pp. 604-611, XP002478298.

Chen et al., "3D Reconstruction of Coronary Arterial Tree to Optimize Angiographic Visualization", IEEE Trans. on medical Imaging, IEEE Service Center, Piscataway, NJ, US, vol. 19, No. 4, Apr. 2000, XP011035955.

Chen et al., "Computer Assisted Coronary intervention by Use of On-line 3D Reconstruction and Optimal View Strategy", Medical Image Computing and Computer-Assisted Intervention, MICCAI, International Conference, Proceed, Oct. 11, 1998, pp. 377-385, XP008026963.

Maddux et al., "Rotational Angiography and 3D Coronary modeling: Revolutions in the Cardiac Cath Lab", Medicamundi Philips Medical Systems Netherlands, vol. 47, No. 2, Aug. 2003, pp. 8-14, XP002478297.

Dumay et al., "Determination of Optimal Angiographic Viewing Angles: Basic Principles and Evaluation Study", IEEE Transactions on Medical Imaging, vol. 13, No. 1, Mar. 1994, pp. 13-24.

Chen et al., "Computer Assisted Coronary intervention: 3D Reconstruction and Determination of Optimal Views", Cardiology Division Dept. of Medicine, Univ. of Colorado Health Sciences Center, Denver, Dept. of Radiology, The University of Chicago, USA, IEEE Computers in Cardiology 1996, pp. 117-120.

Maddux et al., "A Randomized Study of the Safety and Clinical Utility of Rotational Angiography versus Standard Angiography in the Diagnosis of Coronary Artery Disease", Catheterization and Cardiovascular Interventions, in print, 2004.

Movassaghi et al., "A quantitative analysis of 3D coronary modeling from two or more projection images", IEEE Trans. Med. Imag., vol. 12, No. 23, pp. 1517-1531, 2004.

Rasche et al, "ECG-gated 3D Rotational Coronary Angiography", in RSNA, 83rd Scientific Session, pp. C19-382, 2003.

Chen et al., "3D Reconstruction of Coronary Arterial Tree to Optimize Angiographic Visualization", IEEE transaction on medical imaging, vol. 19, No. 4, Apr. 2000.

Chen et al., "Quantitative Analysis of Reconstructed 3-D Coronary Arterial Tree and Intra-coronary Devices", IEEE Trans. Med. Imag. 2002; 21:724-740.

* cited by examiner

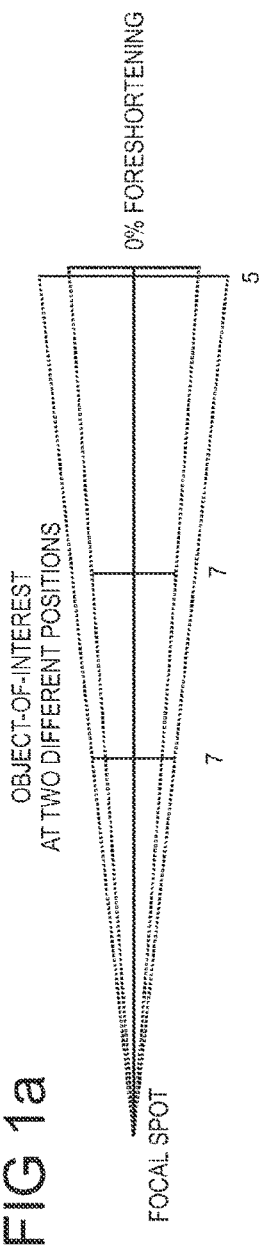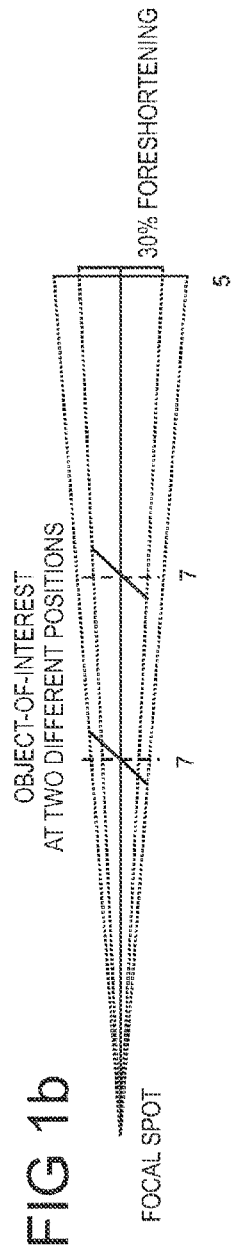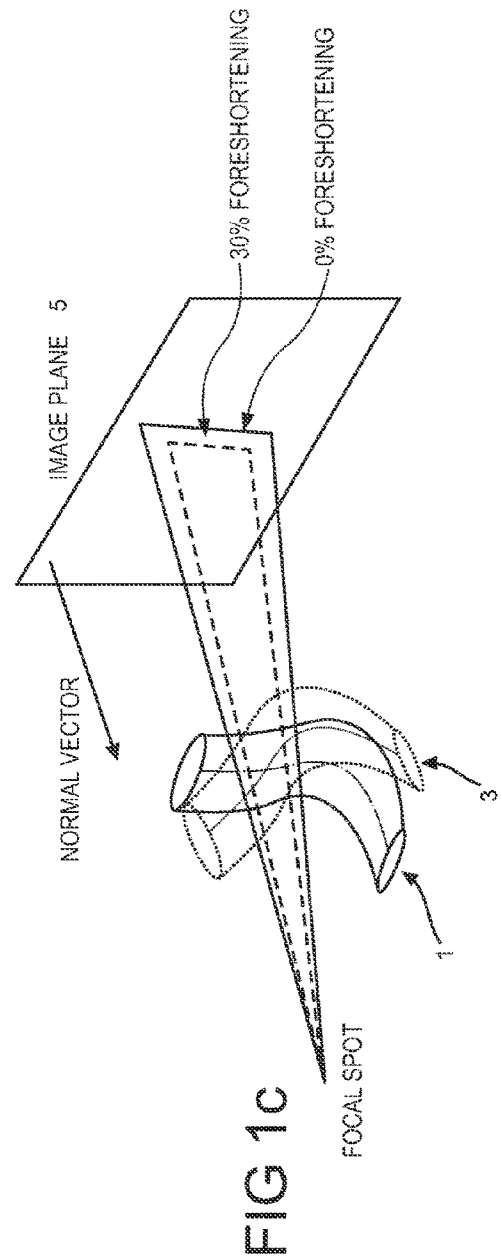

OPTIMAL ROTATIONAL TRAJECTORY DETERMINATION FOR RA BASED ON PRE-DETERMINED OPTIMAL VIEW MAP

The present invention relates to the field of Rotational X-ray Angiography (RA), and more particularly on determining an optimal rotational trajectory of RA based on optimal view maps (OVM).

In interventional neuroradiology, it may be important for the neuroradiologist or angiographer to know, at any time, where the catheter lies within the patient's body, with a millimetric precision. This information is deduced from Digital Subtracted Angiography (DSA) images that he/she mentally links to pre-operative 3-dimensional images (e.g.: Magnetic Resonance (MR) images), thanks to his/her anatomical knowledge.

To day, 3D X-ray rotational angiography (3D-RA) reconstructed volumes are routinely generated from rotational angiography (RA) sequences. Such volumes have been proven to bring an actual supplementary help to the physicians although, DSA remains the cornerstone of interventional neuroradiology. As a consequence, the registration of DSA images with 3D-RA volumes seems to be an extremely promising feature.

Current cath-lab—i.e.: treatment center of coronary artery disease or other blood vessel diseases—interventional procedures such as qualitative stenosis determination, balloon dilatation, stenting etc. are carried out based on 2-dimensional (2D) projection images. In the recent years rotational angiography (RA) has been introduced where a C-arm X-ray system rotates around the patient while acquiring projection images from coronaries filled contrast agent. These data sets can be utilized for diagnostic as described in J. T. Maddux, O. Wink, J. C. Messenger, B. M. Groves, R. Liao, J. Strzelczyk, S. Y. Chen, J. D. Carroll, "A Randomized Study of the Safety and Clinical Utility of Rotational Angiography versus Standard Angiography in the Diagnosis of Coronary Artery Disease", Catheterization and Cardiovascular Interventions, in print, 2004.

The data sets can also be used for 3D coronary modeling as described by B. Movassaghi, V. Rasche, M. Grass, M. Viergever, W. Niessen, "A quantitative analysis of 3D coronary modeling from two or more projection images", IEEE Trans. Med. Imag., vol. 12, no. 23, pp. 1517-1531, 2004.

In addition, the acquired data sets are used also in 3D coronary reconstruction procedures as described by V. Rasche, A. Buecker, M. Grass, R. Suurmond, R. Koppe, H. Kuehl, "ECG-gated 3D Rotational Coronary Angiography", in RSNA, 83rd Scientific Session, pp. C19-382, 2003. The subject-matter of the above-mentioned publications is seen as an integral part of this application and should be included by reference.

The current clinically applied rotational acquisition protocols are chosen based on the experience of the physician and are not subject to any scientific background. Typically, the physician positions the X-ray system at specific coordinates for acquiring a projection image, positions the X-ray system to the next specific coordinates for acquiring the next projection image and so on. Therefore the position determination for acquiring the projection images is not optimized due to differences of human bodies. In order to obtain most accurate 3-dimensional models of coronary trees patient specific positions of the C-arm angiogram system should be used.

The 3-dimensional (3D) character of the coronary artery tree causes a foreshortening of a variety of segments in any projection due to the projection geometry. Therefore, various rotational acquisition protocols include various amounts of projections images with more or less vessel foreshortening and vessel overlap. Foreshortening happens if an object of interest is not positioned in parallel to the projection plane of the X-ray detectors but under a certain angle as can be seen from FIG. 1.

Physicians choose from experimental values and based on experience coordinates in order to reduce foreshortening and overlap of the respective coronal tree of a region of interest (ROI). In practice, more than theoretically required images are taken in order to choose the best image projections for final coronary tree reconstruction. On the other side it is in the interest of the patient to keep the number of acquired projections low in order to keep the exposure of the patient to X-ray at a minimum. On the other side, the physician needs views and image projections in order to reconstruct the best possible 3-dimensional model of a coronary tree for his diagnostic and/or treatment.

S. James Chen and John D. Carroll presented in "3D Reconstruction of Coronary Arterial Tree to Optimize Angiographic Visualization", IEEE transaction on medical imaging, Vol. 19, No. 4, April 2000 a method to determine the quantitative value of the vessel foreshortening and vessel overlap for each arbitrary projection angle based on computer-generated 2D centre-line models derived from the determined 3D centre-line of the coronary arteries for a certain heart phase. The document describes that due to vessel overlap and foreshortening, multiple projections are necessary to adequately evaluate the coronary tree with angiography. Catheter-based interventions can only be optimally performed when these visualization problems are successfully solved. The traditional method provides multiple selected views in which overlap and foreshortening are subjectively minimized based on 2-dimensional (2D) projections. A pair of images acquired from routine angiography studies at arbitrary orientation using a single-plane imaging system was chosen for 3-dimensional (3D) reconstruction. After the arterial segment of interest (e.g., a single coronary stenosis or bifurcation lesion) was selected, a set of C-arm angulations minimizing segment foreshortening was calculated. Multiple computer-generated projection images with minimized segment foreshortening were then used to choose views with minimal overlapped vessels relative to the segment or region of interest (ROI). The optimal views or optimal view maps could then be utilized to guide subsequent angiographic acquisition and interpretation.

This method was even enhanced to generate complete optimal view maps incorporating the 4D (3-D plus time) character of the coronary tree. The so generated optimal view maps (OVM) can be used by the physicians to select a static view with minimal vessel foreshortening and overlap for interventional procedures. Typically, the generated optimal view maps are in color. Light areas typically indicate regions of minimal foreshortening and/or overlap. In the example of FIG. 2 white areas illustrate regions with 0-10% foreshortening or overlap. So, these positions of an angiogram system represent the optimal position relative to the body of a patient in order to generate image projections for the best 3-dimensional reconstruction of coronary trees or parts thereof.

The vessel overlap can be determined based on the method described in "Quantitative analysis of reconstructed 3-D coronary arterial tree and intra-coronary devices" by Chen S Y J, Carroll J D, Messenger J C, published in IEEE Trans. Med. Imag. 2002; 21:724-740. The overlap value for a specific vessel segment $C^k$, is defined as a propagation of overlap relative to all other arteries $C^i$:

$$\circ\{OVM\} = \sum_{i=1, i \neq k}^{n} \frac{\Pi_{\alpha,\beta}(C^i) \cap \Pi_{\alpha,\beta}(C^k)}{\Pi_{\alpha,\beta}(C^k)} \cdot 100\%, \quad (1)$$

wherein $C^i$ and $C^k$ denote the 3D arterial lumen of the ith artery and the selected segment of interest at the kth artery, respectively. $\Pi_{\alpha,\beta}$ (C) denote an operator that counts the number of pixel after projecting the object C onto the image plane based on the C-arm angles ($\alpha$, $\beta$).

However, the problem of determining an optimal set of acquired image projections still exist because the current clinically applied rotational acquisition protocols are chosen based on the experience of the physician.

Hence there may be a need for a method to determine an optimal rotational run of a C-arm X-ray system for acquiring projection images with minimal vessel foreshortening and minimum vessel overlap for a region of interest.

According to a first aspect of the invention there is provided a method for determining an optimal trajectory for rotational X-ray angiography for vessel like structures with a C-arm X-ray system
having at least two degrees of freedom defined by
  a propeller-type motion of the C-arm expressed in left/right coronary artery oblique angle $\alpha$, and
  a roll motion of the C-arm expressed in a caudal/cranial angle $\beta$
comprising the following steps:
(a) generation of a 3-dimensional representation of a centreline of a body vessel of a region of interest;
(b) generation of an optimal view map limited in a x- and y-direction by maximal values of $\alpha$ and $\beta$ and/or selecting preferred viewing angles determined by a clinician; and
(c) calculation of an optimal trajectory for the C-arm of the X-ray system within the limits of the optimal view map, wherein an optimal trajectory is at least determined by movements of the C-arm within its two degrees of freedom allowing image projections with minimal foreshortening and overlap of the while minimizing the regions of interest's exposure to X-rays.

The described method may have the advantage, to determine automatically an optimal trajectory for rotational angiography for C-arm X-ray systems in terms of minimum vessel foreshortening and vessel overlap, insuring 2-dimensional angiograms with optimal diagnostic value and/or optimal 3-dimensional reconstructed image quality. Regions of interest are typically specific vessel segments or a complete coronary tree of a patient. Any other body vessel could also be a region of interest. Those regions include coronary arteries, coronary vanes or vessels or structures inside the head. It should explicitly be mentioned that none vessel inside a patient's body should be excluded for use of the claimed method. The method could be applied to any part of a living subject.

The currently used trajectories or C-arm positions are based on the experience of physicians and cannot guarantee optimized image projections and consequently do not deliver the required quality of the images for the physician. This limits the value of image projections or reconstructed coronary trees or parts thereof to the physician.

The inventive method makes use of modern X-ray angiogram systems that can move the C-arm of the angiogram system in two degrees of freedom at the same time. This is required in order to enable any possible trajectory of the X-ray system within the limits of the C-arm mechanics. Traditionally, 3D-RA systems (3-dimensional X-ray angiogram systems) allowed the rotation around only one angle at a time. The C-arm allows a propeller-type motion wherein clinical relevant angles range from 120° LAO (left artery oblique) to 120° RAO (right artery oblique). In addition, a roll motion of the C-arm is possible as well. Clinical relevant angles range from 60° CRAN (cranial angle) to 60° CAUD (caudal angle). This is equivalent to a rotation by +/−60° around the middle position of the C-arm in respect to is pivot point or center of rotation.

Step (b) of the claimed method allows two alternative option: Either an optimal view map is generated or a clinical has his/her own set of optimal viewing angles that he would go and make images from. An optimal trajectory could then be computed to visit these points expressed in viewing angles. In addition there could be a consensus between a number of clinicians on a trajectory that would optimally serve their needs.

According to another aspect of the invention an X-ray C-arm system is provided with the ability to run a trajectory determined according to the method for determining an optimal trajectory for a rotational X-ray coronary angiography.

According to yet another aspect of the invention a computer system for calculating a trajectory is provided according to the method for determining an optimal trajectory for a rotational X-ray coronary angiography and controlling the motion of C-arm X-ray angiogram system.

A further aspect of the inventions is to provide a computer program product with instructions for calculating a trajectory according to the method for determining an optimal trajectory for a rotational X-ray coronary angiography and controlling the motion of a combined C-arm X-ray angiogram system.

Another aspect of the invention is to provide a computer readable medium storing a set of instructions for a computer system and being able to calculate a trajectory according to the method for determining an optimal trajectory for a rotational X-ray coronary angiography and control the motion of a combined C-arm X-ray angiogram system.

The above mentioned aspect have the advantage to let a RA system run fully automated a trajectory for providing optimal image projections with the least possible foreshortening and/or overlap of vessels In one embodiment of the invention the step of determining of an optimal trajectory comprises the steps of minimizing the following equation:

$$F(\kappa, \lambda, \alpha, \beta) = \sum_{\alpha=-120}^{\alpha=120} \sum_{\beta=-60}^{\beta=60} \kappa f(\alpha, \beta) + \lambda O(\alpha, \beta) \quad (2)$$

wherein:
  $\kappa$ is a weighting parameter;
  $\lambda$ is a weighting parameter;
  $\alpha$ is an angle value of the left respectively right coronary artery oblique;
  $\beta$ is an angle value of the caudal respectively cranial angle;
  $f(\alpha, \beta)$ is a function associated with a vessel foreshortening; and
  $O(\alpha, \beta)$ is a function associated with a vessel overlap.

$\kappa$ and $\lambda$ are parameters typically varying from 0 to 1, and according to a further embodiment of the invention their mathematical sum is 1.

In one embodiment, the C-arm of the angiogram system is mounted to a L-arm resulting in a combined L-arm/C-arm angiogram system enabling one additional degree of freedom giving the angiographer much more flexibility in positioning the angiogram system relative to the patient.

In another embodiment, the step of generating of a 3D representation of a centre-line of a vessel in a region of interest comprises a modeling approach that is based on two or more acquired projection images. As mentioned above these projection images can be acquired by the method described in "A quantitative analysis of 3D coronary modeling from two or more projection images", IEEE Trans. Med. Imag., vol. 12, no. 23, pp. 1517-1531, 2004, by B. Movas-saghi, V. Rasche, M. Grass, M. Viergever, W. Niessen. The subject-matter of this document should also be incorporated by reference.

A further embodiment, of the invention uses for the step of generating a 3-dimensional representation of a centre-line of an area of interest comprises a modeling approach based on pre-acquired images data sets of different modalities. Hence this embodiment is making use of pre-acquired data sets from previous investigations. Two types of data sets should be mentioned as examples. Computer tomography (CT) scans and magnetic resonance (MR) data sets. These data are often available for patients with heart diseases and can be reused.

In yet another embodiment, the step of generating a representation of a centre-line of a vessel in a region of interest comprises a modeling approach based on pre-acquired 3-dimensional rotational angiography images based on non-optimal arbitrary acquisition trajectories. These images might have been acquired based on the experience of a physician as discussed above. Some of these images might be good enough for the planned treatment of a patient but they represent point-data with no guarantee that they represent the best available data in order to reconstruct 3-dimensional models of vessels.

There is another way to perform the step of generating a 3-dimensional representation of a centre-line of a vessel in a region of interest. In this embodiment this step comprises a modeling approach based on a phantom model representing an average of human coronaries. A well know phantom model is the Dudge model that includes the experience gained from about two dozen patients. The model is an abstract model that averages out variations between different test persons. However, also this model does not deliver a perfect phantom model.

It has to be noted that embodiments of the invention have been described with reference to different subject matters. In particular, some embodiments have been described with reference to apparatus type claims whereas other embodiments have been described with reference to method type claims. However, a person skilled in the art will gather from the above and the following description that, unless other notified, in addition to any combination of features belonging to one type of subject matter also any combination between features relating to different subject matters, in particular between features of the apparatus type claims and features of the method type claims is considered to be disclosed with this application.

On the basis of the above given and the following explanation of the method for determining an optimal trajectory for a rotational X-ray coronary angiography for a combined C-arm X-ray or a combined L-arm/C-arm system a skilled person will we able to translate the steps of the method into a computer program for carrying out the method.

The aspects defined above and further aspects of the present invention are apparent from the examples of embodiment to be described hereinafter and are explained with reference to the examples of embodiment. But the invention should not be limited to these examples.

The illustrations in the drawings are schematically. It should be noted that in different figures, similar or identical elements are provided with the same reference signs. The figures show:

FIG. 1a is a the schematic diagram of 0% foreshortening of vessels;

FIG. 1b is a the schematic diagram of 30% foreshortening of vessels;

FIG. 1c is a the schematic diagram illustrating 0% and 30% foreshortening of a vessel in a 3-dimensional view;

Figure 10A:
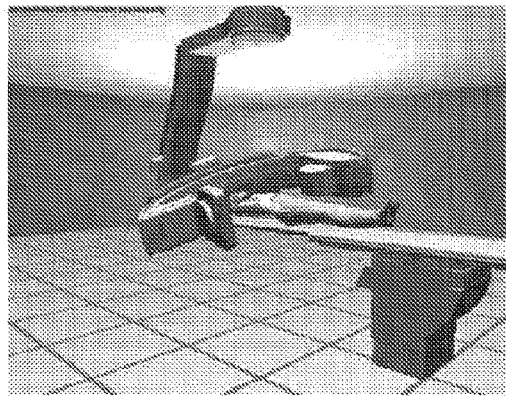
Figure 10D:
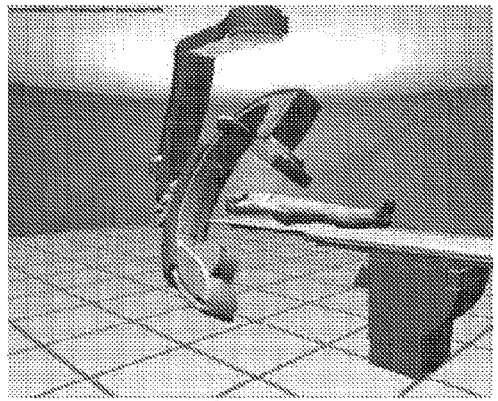
Figure 10B:
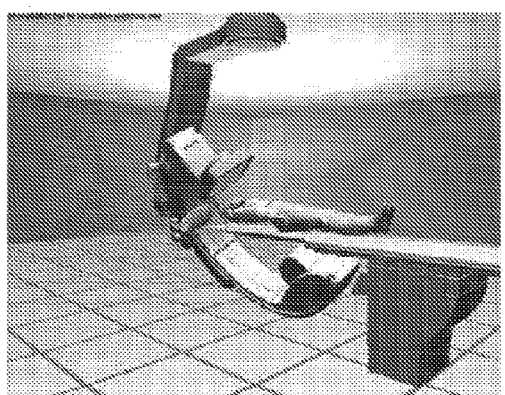
Figure 10E:
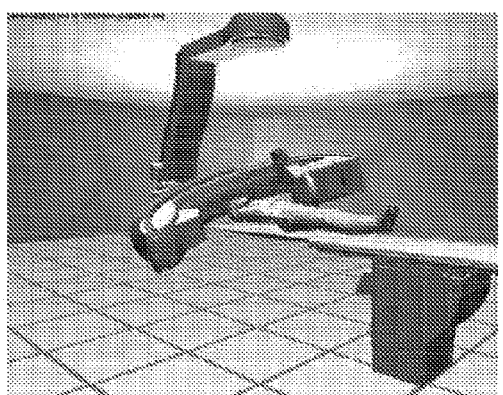
Figure 10C:
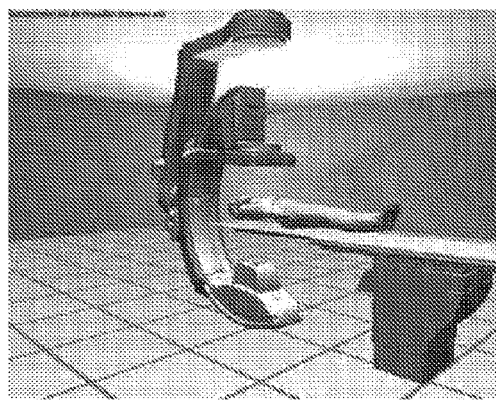
Figure 10F:
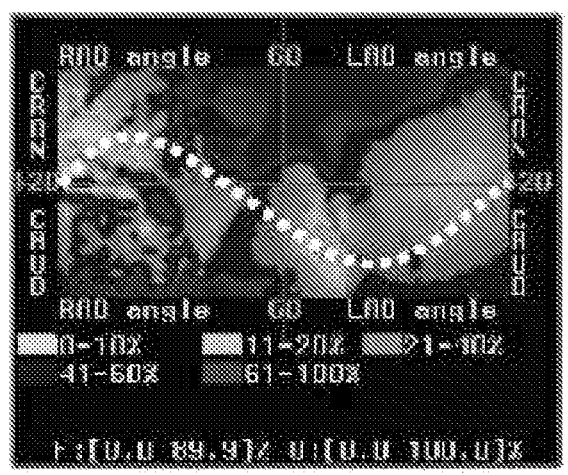
Figure 11:
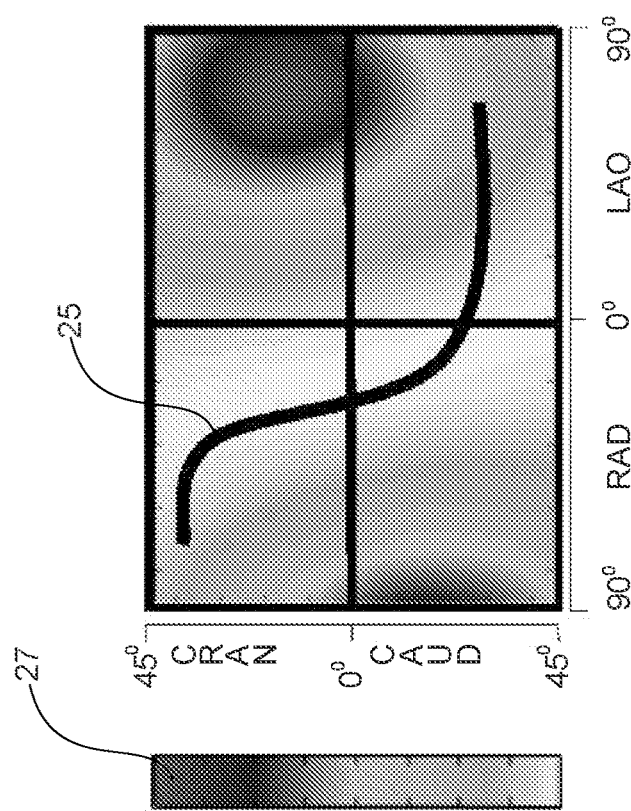

FIG. 7a-f are illustrations of a rotational roll acquisition trajectory of a C-arm angiogram system combined with an illustration of a trajectory through an OVM;

FIG. 8a-f are illustrations of a tilted propeller-type rotational run of a C-arm angiography system combined with an illustration of a trajectory through an OVM;

FIG. 9a-f are illustrations of a roll motion of a C-arm angiography system combined with an illustration of a trajectory through an OVM under the condition of a fixed propeller-type position and with the L-arm positioned 90° to the right;

FIG. 10a-f are illustrations of a dual motion acquisition with simultaneous roll and propeller motion of the C-arm of a 3D-RA system combined with an illustration of a trajectory through an OVM; and FIG. 11 is an illustration of a determined optimal trajectory of the C-arm system though an optimal view map.

Figure 12:
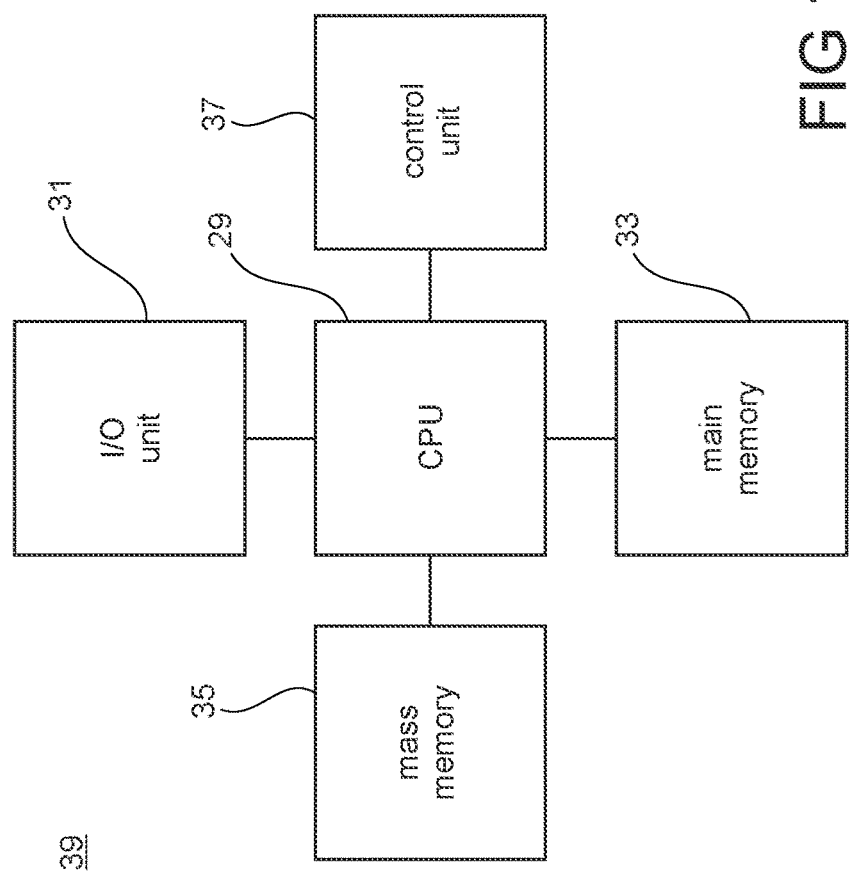

FIG. 12 shows a simplified computer system according to an exemplary embodiment of the present invention which may be used as control unit for an x-ray system according to an exemplary embodiment of the present invention.

For certain treatment and diagnostic steps physicians need the best model for a blood vessel, i.e.: the coronary vessel system. A key problem is foreshortening of vessels as illustrated by FIGS. 1a, 1b and 1c. A projection of a 3-dimensional vessel produces different projections in a 2-dimensional projection image as typically generated by X-ray angiogram systems. A blood vessel is shown in two positions 1 and 3 in FIG. 1c. The projection reaches its largest value if the vessel portion to be projected is in parallel to the image plane 5. In case an angle between the vessel's or vessel portion's longitudinal axis and the image plane is greater than 0, the projection is shortened by a factor of 30% in the example of FIG. 1c. The FIGS. 1a and 1b show the effect in a 2-dimensional schematic diagram. The projections of the objects 7 are shortened by the effect of foreshortening depending on different distances and angles between the object 7 and the image plane 5. The example of FIG. 1a would deliver the best image projection with 0% foreshortening.

Figure 3A:
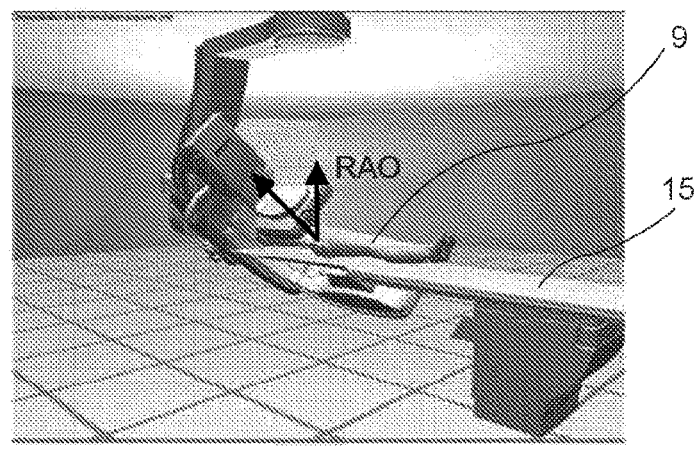
FIG. 3a is a combined L-arm/C-arm angiogram system visualizing the meaning of right artery oblique angle (RAO)
Figure 3B:
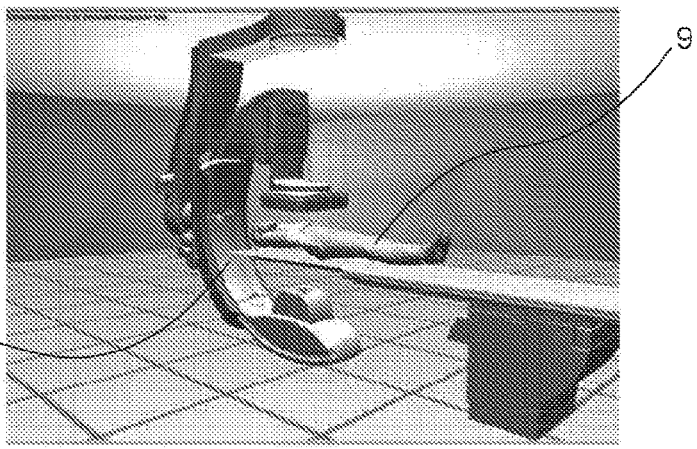
FIG. 3b is a combined L-arm/C-arm angiogram system with all possible movement angles in a neutral middle position.
Figure 3C:
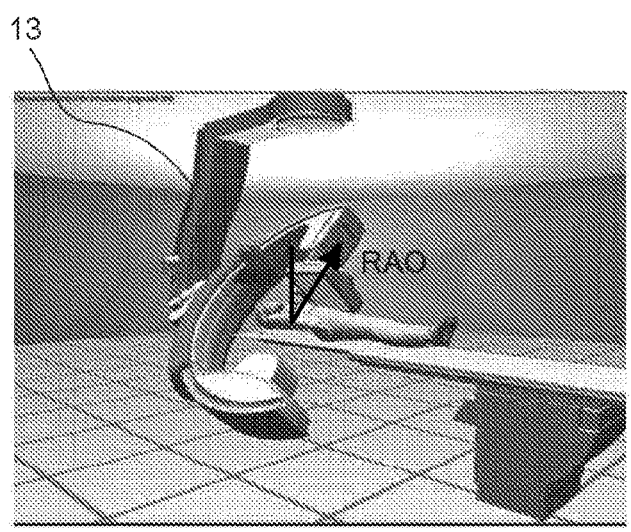
FIG. 3c is a combined L-arm/C-arm angiogram system visualizing the meaning of left artery oblique angle (LAO)

FIGS. 3a, 3b, 3c and FIGS. 4a, 4b, 4c explain movements of a typical C-arm angiogram system. A patient is lying flat on a support 15. The longitudinal axis of the body of the patient forms a natural axis for orientation. The C-arm 11 is mounted with its pivotal point on the line or close to the line of the longitudinal axis of the patient if the angiogram system is in a neutral position as shown in FIG. 3b. The C-arm 11 can rotate in a propeller-type motion around this pivotal point. The angles—measured from a neutral position shown in FIG. 3b—are typically named RAO (right anterior oblique) as shown in FIG. 3a which means a counter clockwise rotation seen from the feet of the patient, and LAO (left anterior oblique) as shown in FIG. 3c which is a turn in the opposite direction compared to a RAO angle rotation. In addition, an L-arm 13 is illustrated. The L-arm 13 carries the C-arm 11 of the angiogram system and is in a neutral middle position.

The focal point of the angiogram system, i.e. the X-ray sender and the X-ray receiver array or image plane, is positioned at the respective ends of the C-arm 11, moving with the C-arm 11 as is well known in the art. The region of interest (ROI), i.e. the heart of a patient, stays typically in a constant position during a working cycle of the angiogram system.

Figure 4A:
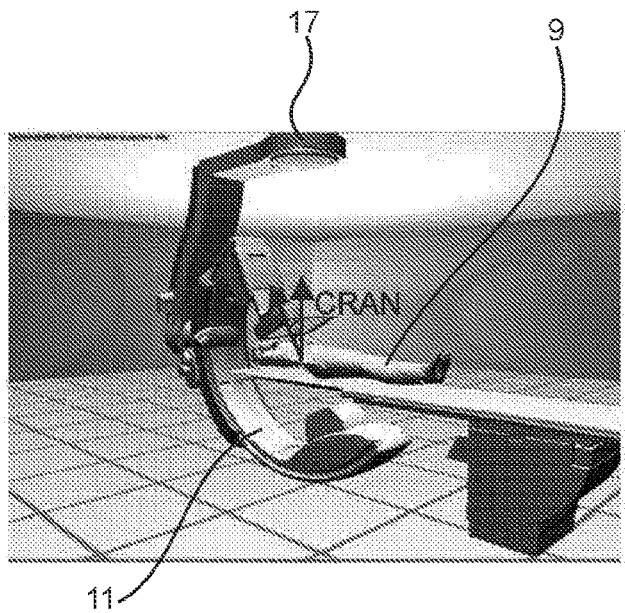
FIG. 4a is a combined L-arm/C-arm angiogram system visualizing the meaning of cranial angle (CRAN)
Figure 4B:
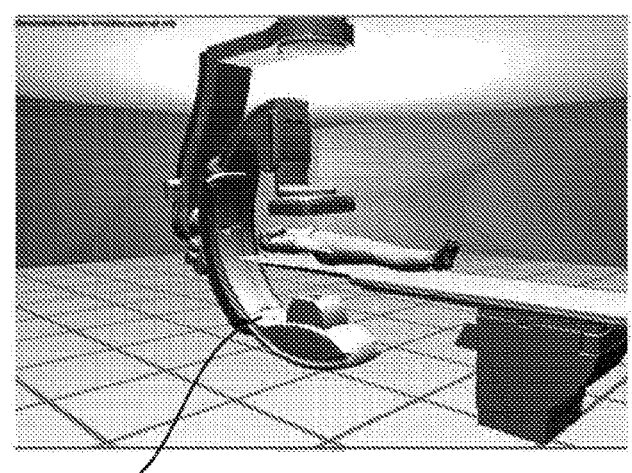
FIG. 4b is a combined L-arm/C-arm angiogram system with all possible movement angles in a neutral middle position.
Figure 4C:
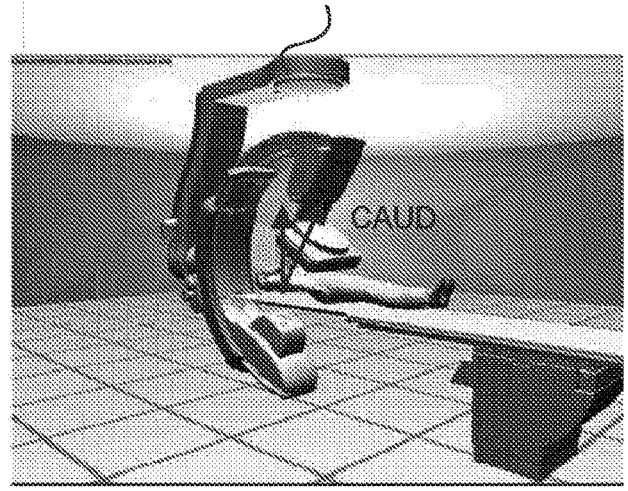
FIG. 4c is a combined L-arm/C-arm angiogram system visualizing the meaning of caudal angle (CRAD)

FIGS. 4a, 4b and 4c illustrate another possible movement of the C-arm 11. It is a roll motion. This movement is measured with the angles CRAN (cranial angle) and CAUD (caudal angle). They are typically up to 60° from the middle position. Assumed the C-arm 11 starts from the neutral position as shown e.g. in FIG. 3b or 4b the movement of the ends of the C-arm 11 is in a plane defined by the longitudinal axis of the patient and the gravity vector.

Figure 5A:
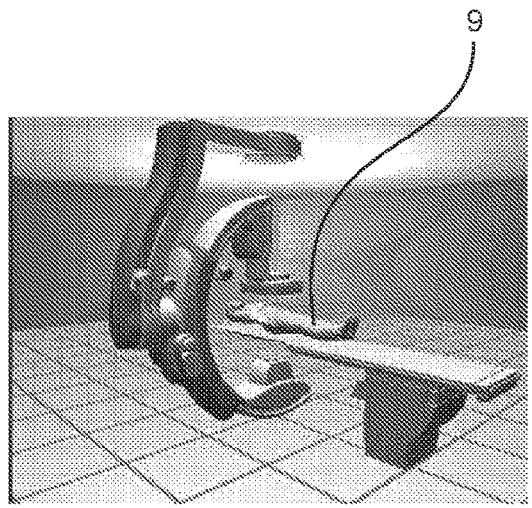
FIG. 5a is a combined L-arm/C-arm angiogram system illustrating the rotational movement of the L-arm by 90° to the left.
Figure 5B:
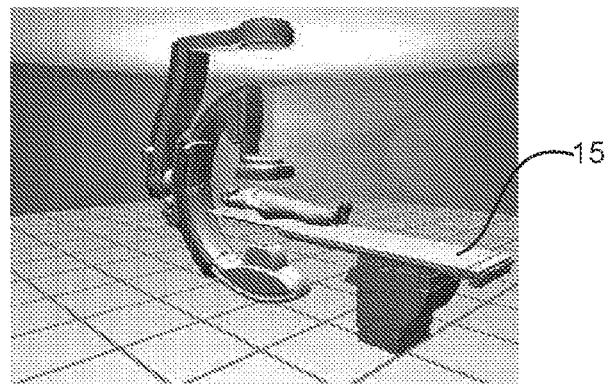
FIG. 5b is a combined L-arm/C-arm angiogram system with all possible movement angles in neutral a middle position.
Figure 5C:
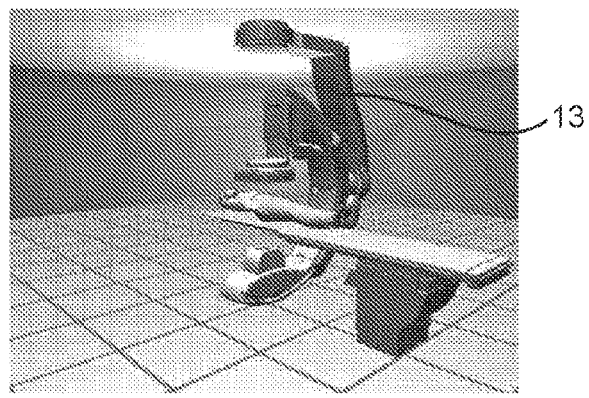
FIG. 5c is a combined L-arm/C-arm angiogram system visualizing the rotational movement of the L-arm by 90° to the right.

Finally, a modern angiogram system can also rotate the L-arm 13 around a pivotal point at the top 17 of the L-arm 13. This rotational axis is defined between mounting means at the ceiling of the investigation room and the L-arm 13. A typical movement of the L-arm 13 is 90° to the left as illustrated in FIG. 5a or 90° to the right as illustrated in FIG. 5c. FIG. 5b again shows the neutral position of the total system.

The angiogram system as explained represents a system with three degrees of freedom: two are defined by the possible movements of the C-arm 11 and one is defined by the rotation of the L-arm 13. However, the method discussed herein is not limited to an angiogram system with three degrees of freedom. It also works with two degrees-of-freedom-movement of the C-arm of conventional angiogram systems. The L-arm 13 could be seen as fixed in this case. With such a setup the inventive method could also be executed with embodiments of angiogram systems like floor movable angiogram systems that are not mounted at the ceiling of a room.

Figure 2:
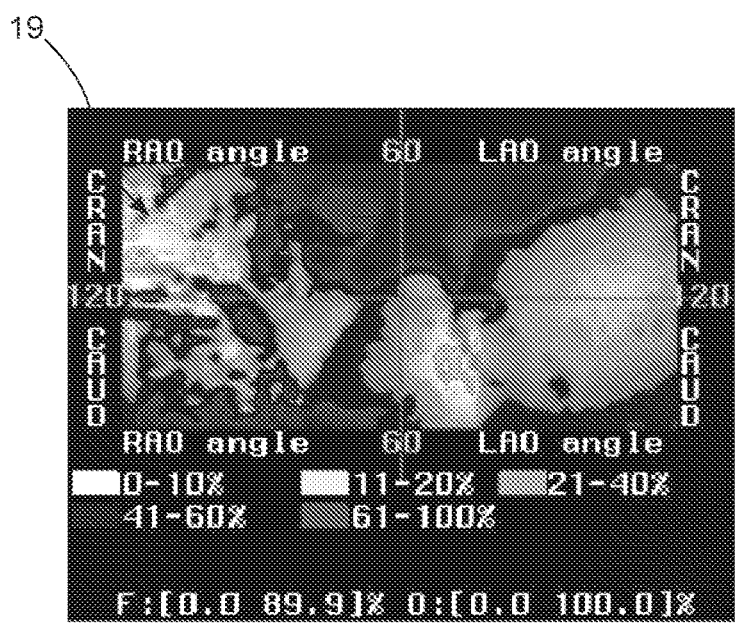
FIG. 2 is an example of an optimal view map of a specific vessel—different grey shades show different foreshortening and/or overlap values.

A typical result of an angiogram system is demonstrated in FIG. 2. It is an optimal view map (OVM). OVMs are typically in colour, wherein each pixel is a representation of an overlap or foreshortening value in the ROI between 0 and 100%. Each pixel of the OVM is represented by two angle values: a pair of RAO/LAO defining the x-direction in the chart of FIG. 2 and a pair of CRAN and CAUD defining the y-axis of the chart. FIG. 2 is a black and white translation of the original coloured chart of the OVM. There are light-coloured areas and dark areas on the OVM according to FIG. 2. Simply said, the light-coloured regions represent regions of low foreshortening and/or overlap of vessels, while darker regions represent regions of higher values of foreshortening and/or overlap.

This means that for a given angle pair, e.g., RAO=LAO=0° and CRAN=30°, the result for getting good image reconstruction for a 3-dimensional model built out of 2-dimensional projection images produced by the angiogram system would be much worse than for a RAO/LAO and CRAN/CAUD combination resulting in a light-coloured area, e.g. RAO=100° and CRAN=30°, which is represented by numeral 19 in FIG. 2.

This means for the physician that if he wants to have the optimal position for the C-arm angiogram system to produce the best 3-dimensional reconstructions of a vessel, e.g. coronary blood vessels, for diagnostic or treatment purposes he would position the C-arm 11 to an area within a white area in the OVM.

Figure 6A:
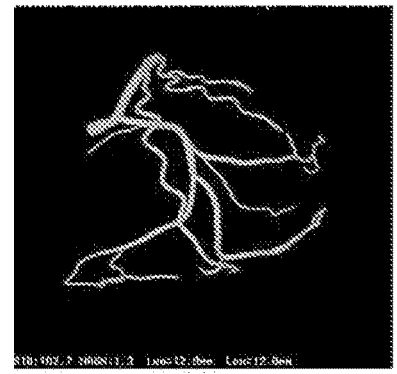
FIG. 6a is a suboptimal view of a modeled LCA (left coronal artery)
Figure 6B:
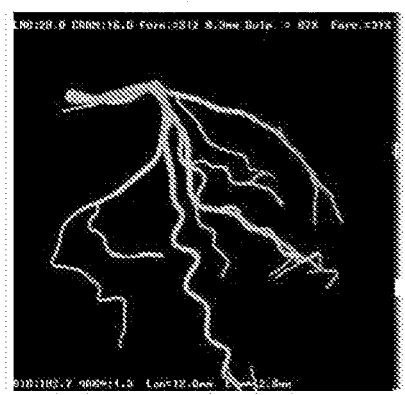
FIG. 6b is a view of the modeled LCA from a nearly perfect perspective.

FIGS. 6a and 6b show examples of a 3-dimensional model of a blood vessel tree. FIG. 6a is a bad example because the physician cannot really imagine how the vessel tree would look like in reality. FIG. 6b is a much better 3-dimensional model generated of image scans. In FIG. 6b the 3-dimensional model allows much better interpretation of the real coronary tree because of a very much reduced values for foreshortening and overlap.

Figure 6C:
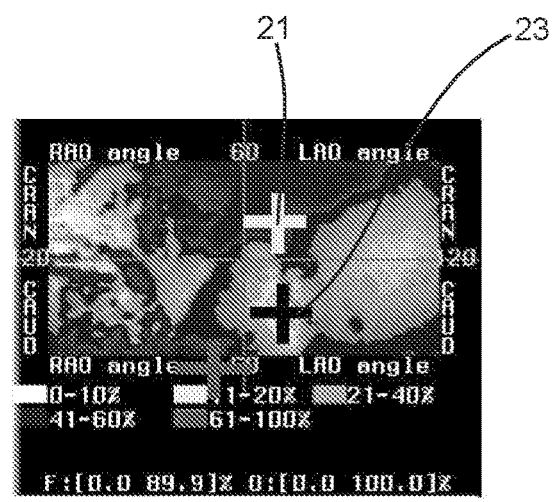
FIG. 6c is an optimal view map of the positions for the modeled LCA from FIGS. 6a and 6b.

In this context, the white cross 21 in FIG. 6c could represents a RAO/LAO and CRAN/CAUD combination of a bad position for the C-arm 11, assumed the physician wants to obtain the best possible image projections for reconstructing a 3-dimensional model of the vessel system. The 3-dimensional model that results in the vessel tree as shown in FIG. 6b would relate to the black cross 23 in FIG. 6c. It represents a much better position for images taken by the angiogram system to get the best interpretable 3-dimensional model of the vessel tree, because it has much less foreshortening and overlap.

Figure 7A:
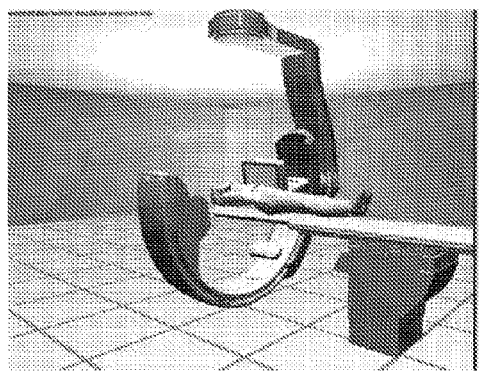
Figure 7D:
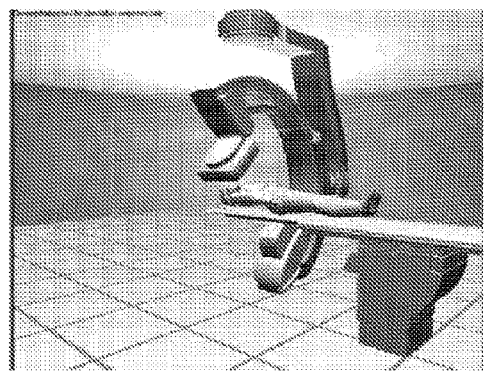
Figure 7B:
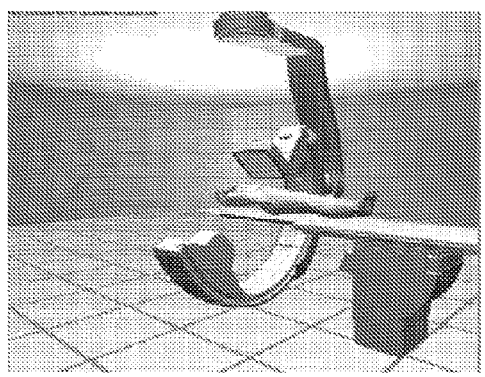
Figure 7E:
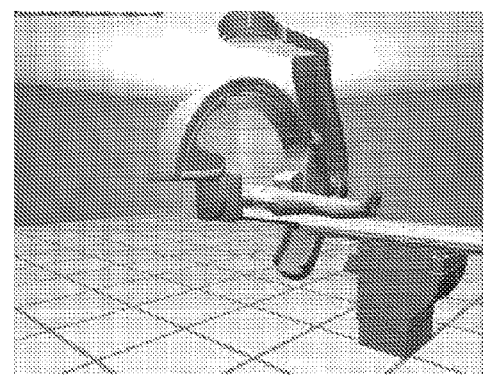
Figure 7C:
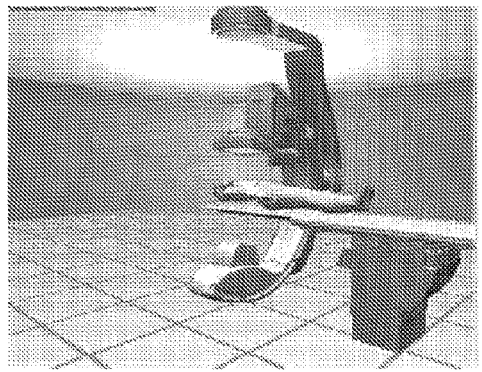
Figure 7F:
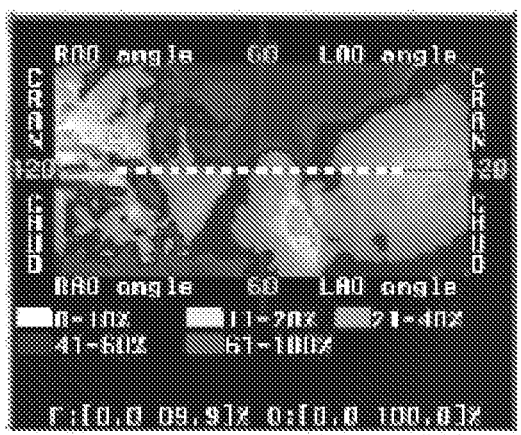

Now, referring to FIG. 7a to 7e the movement of the C-arm 11 and the position of the OVM should be discussed. Because the L-arm 13 is moved 90° to the left the roll motion of the C-arm 11 does not represent a rotation in LAO/RAO direction as it would be the case for a neutral middle position of the L-arm 13. This is because the coordinate system must be interpreted from the view of the patient of the ROI. Because of the L-arm 13 orientation the X.-ray sender/detector at the end of the C-arm 11 moves in a CRAN/CAUD direction seen from the patient. Hence by moving the L-arm 13 by 90° the LAO/RAO and CRANM/CAUD direction are exchanged by each other. On the OVM of FIG. 7f this results in a movement along the x-axis as indicated by the horizontal white dotted line. FIG. 7c represents the mid point of the OVM with LAO/RAO=0° and CRAN=CAUD=0°. The positions in FIGS. 7a and 7e would mark the end points of the white line in FIG. 7f.

Figure 8A:
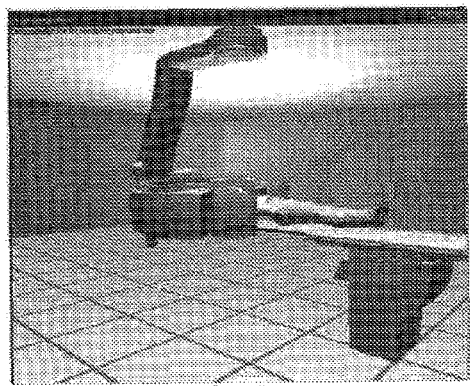
Figure 8D:
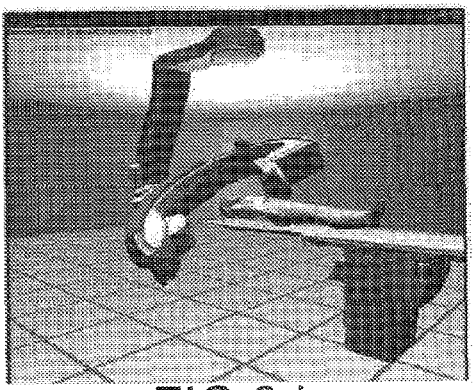
Figure 8B:
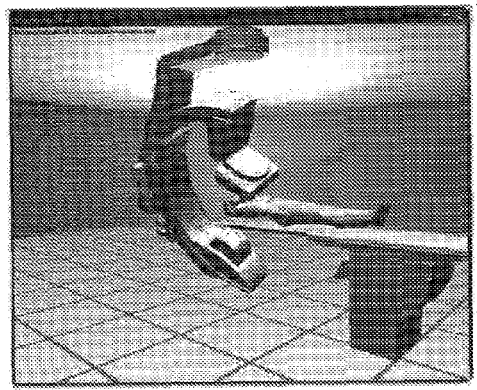
Figure 8E:
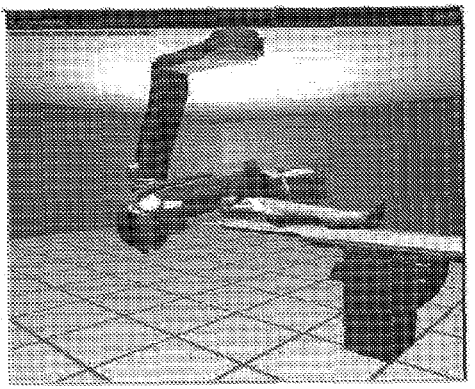
Figure 8C:
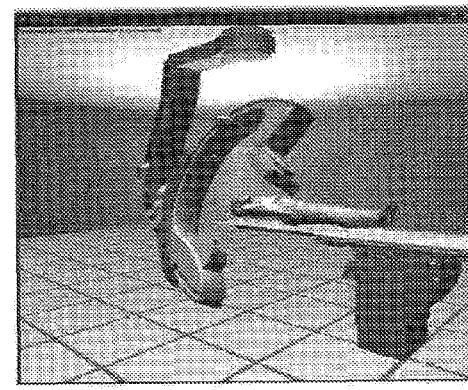
Figure 8F:
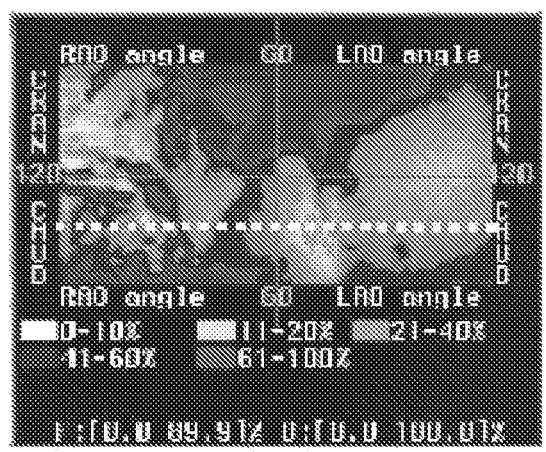

A similar result, i.e. a trajectory over the OVM, is illustrated in FIG. 8f. Here the L-arm 13 is again in the neutral middle position. The C-arm 11 made a roll motion and keeps this fixed at CAUD=30° while the C-arm 11 performs a propeller-type motion around the ROI. This results in the white dotted line on the OVM in FIG. 8f. It should be noted that the positions shown go roughly from RAO=90° to LAO=90° while the chart of FIG. 8f shows the line going from RAO=120° to LAO=120°. But this does not change the fundamental principle of a straight line on the OVM. It could also be noted that the trajectory of the C-arm 11 moves over regions of little foreshortening and overlap at about CAUD=30° and LAO about 10° to 20° indicated by light areas. However, also dark regions are crossed on the OVM by the motion of the C-arm 11 so that an optimal trajectory is not performed in terms of minimizing equation (2).

Figure 9A:
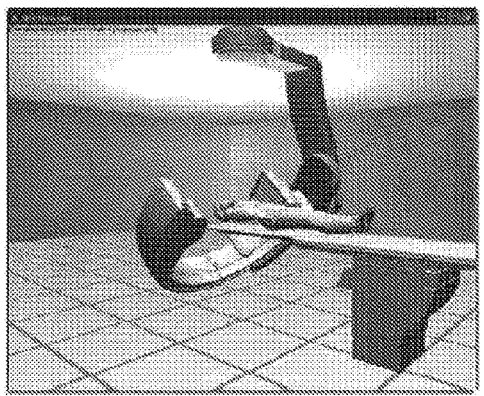
Figure 9B:
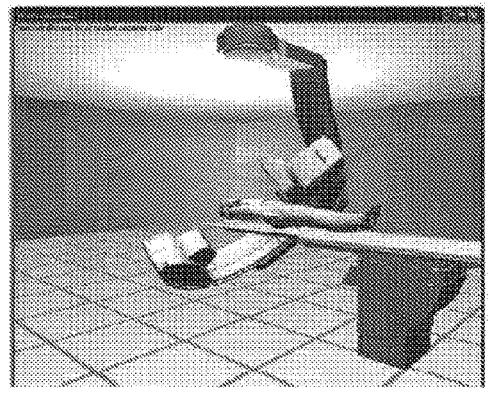
Figure 9C:
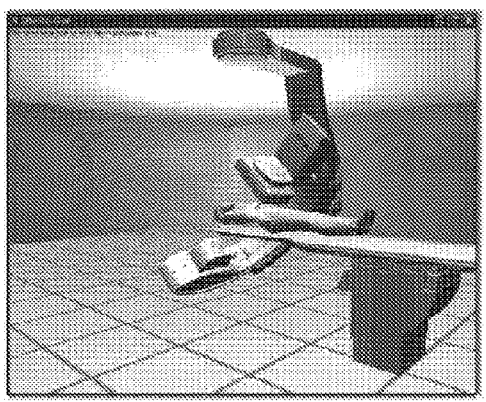
Figure 9D:
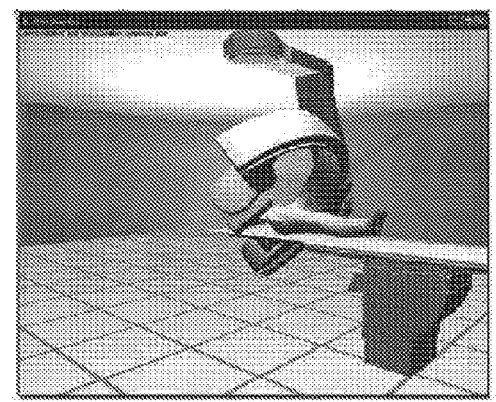
Figure 9E:
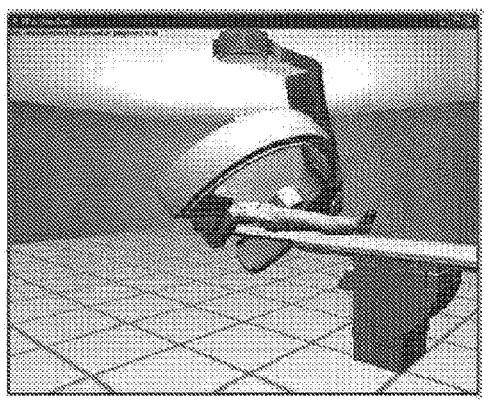

FIG. 9a to FIG. 9f illustrate a simulated combined motion in both degrees of freedom of the C-arm of the angiogram system. In FIG. 9a LAO is about 90° and CRAN is about 10°. The motion of the C-arm 11 would in principle result in the white dotted line of FIG. 9f. It should be noted that FIG. 9a to FIG. 9e are not exactly correlated to the trajectory that results in the white line of FIG. 9e that starts with RAO=120°, crosses the y-axis at about CAUD=30° and finishes on the right side of FIG. 9e with LAO=120° and CRAN=CAUD=0°. However, it is important to realize that the C-arm angiogram system is able to run such a trajectory. It should also be noted that the trajectory—indicated by the white dotted line—of the angiogram system in FIG. 9f moves across light-coloured and dark regions of the OVM.

Figure 9F:
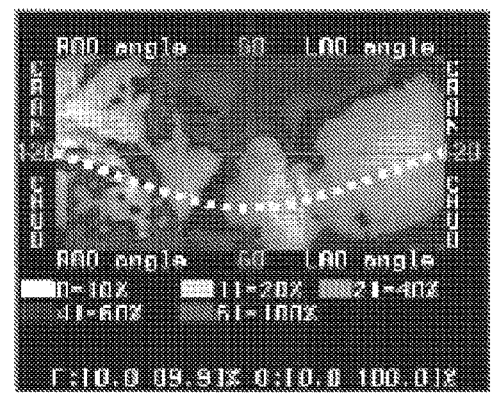

This would mean that the trajectory chosen is not optimal seen from the perspective of minimal overlap and foreshortening, because not all light areas of the OVM of FIG. 9f are crossed by the trajectory.

This is different in FIG. 10f. Here the white dotted line is the result of a dual motion of the C-arm 11 according to FIGS. 10a to 10e. The angle movement of the C-arm angiogram system is manipulated in a way that more than one white area of the OVM as illustrated by FIG. 10f is crossed.

FIG. 11 finally illustrates another optimal trajectory 25 of the C-arm 11. The trajectory taken moves more or less only in the white areas of the underlying OVM. It moves basically from quadrant 1 on the upper left side of the OVM through quadrant 4—which is defined as the lower left quadrant of the OVM—to quadrant 3 which is defined as the lower right quadrant. The trajectory neither touches nor comes near regions of high overlap and/or foreshortening symbolized by dark regions of the OVM. One of those areas is illustrated as a dark spot in quadrant 2 of the illustrated OVM which is defined as the upper right quadrant. The scale 27 on the left side of the chart explains the degrees of overlap and/or foreshortening. As can be seen the trajectory only lies in areas with overlap and foreshortening below 10%.

The trajectory taken is based on the inventive idea to minimize equation (2) as explained above. The calculation has of course to take into account the physically limiting factors of an actual angiogram system.

FIG. 12 illustrates a computer system 39 according to an exemplary embodiment of the present invention to perform a method according to an exemplary embodiment of the present invention. A software according to an exemplary embodiment of the present invention may cause the computer system to perform the method steps of an exemplary embodiment of the present invention, the computer system comprising a central processing unit 29 for all processing purposes, an input output device 31, a main memory 33, a mass memory 35 and a control unit 37. The input/output unit 31 includes typically a keyboard for inputting commands into the computer system and a visualization device such as a computer screen or any other display. The main memory 33 works in combination with the CPU supporting the CPU while storing executable commands for the CPU or data value. The setup of these components is equivalent to a Von-Neumann-machine which is well known in the art. The mass memory 37 can store mass data like image data obtained or received from a C-arm X-ray system or any other data, commands and program code. The optional control unit which is not part of a classical Von-Neumann-machine can control the engines and other devices of a C-arm X-ray system or receive data from various detectors. This way the movement of the C-arm of the X-ray angiogram system can be controlled and monitored. The computer system 39 can also have communication links to other electronic devices required to support X-ray angiographers. These communicating links can be connected to the input/output unit 31 or the control unit 37. Other connections types to other electronic systems are optional and well known in the art.

It should be noted that the term "comprising" does not exclude other elements or steps and the "a" or "an" does not exclude a plurality. Also elements described in association with different embodiments may be combined. It should also be noted that reference signs in the claims should not be construed as limiting the scope of the claims.

In order to recapitulate the above described embodiments of the present invention one can state that the central idea is to determine a trajectory for a C-arm angiogram system or 3D-RA system starting from known optimal view maps. The trajectory of the C-arm 11 through an OVM is manipulated in such a way as to cross only regions of minimal foreshortening and overlap. This results finally in the best possible image projections for 3-dimensional reconstruction of a coronary tree or other vessels or part thereof or 2-dimensional image projections for treatments.

LIST OF REFERENCE SIGNS

1 Blood vessel position
3 Blood vessel position
5 Image plane of projection
7 Projection object
9 Patient
11 C-arm
13 L-arm
15 Support
17 Top point of L-arm
19 OVM region with little foreshortening and overlap
21 White cross
23 Black cross
25 Optimal trajectory for C-arm
27 Grey scale for overlap and foreshortening
29 central processing unit
31 input/output unit
33 main memory
35 mass memory
37 control unit
39 computer system

The invention claimed is:

1. A method for determining an optimal trajectory for rotational X-ray angiography for vessel like structures with a C-arm X-ray system,
wherein a C-arm of the C-arm X-ray system has at least two degrees of freedom defined by
a rotational, propeller-type movement of the C-arm expressed in a right or left coronary artery oblique angle α, and
a roll motion of the C-arm expressed in a caudal or cranial angle β, the method comprising the acts of:
generating by a processor a 3-dimensional representation of a centre-line of a body vessel in a region of interest;
generating an optimal view map;
displaying the optimal view map on a display; and
calculating an optimal trajectory, wherein the optimal trajectory is at least defined by movements of the C-arm within its at least two degrees of freedom allowing image projections with minimal foreshortening and/or overlap while minimizing an exposure of a region of interest to X-ray, wherein the act of calculating an optimal trajectory comprises the acts of minimizing the following equation:

$$F(\kappa, \lambda, \alpha, \beta) = \sum_{\alpha=-120}^{\alpha=120} \sum_{\beta=-60}^{\beta=60} \kappa f(\alpha, \beta) + \lambda O(\alpha, \beta)$$

wherein:
$\kappa$ is a weighting parameter;
$\lambda$ is a weighting parameter;
$\alpha$ is an angle value of the left or right coronary artery oblique angle;
$\beta$ is an angle value of the caudal or cranial angle;
$f(\alpha, \beta)$ is a function associated with a vessel foreshortening; and
$O(\alpha, \beta)$ is a function associated with a vessel overlap.

2. The method according to claim 1, wherein the weighting parameters $\kappa$ and $\lambda$ fulfill the following equation:

$\kappa + \lambda = 1$.

3. The method according to claim 1, wherein
the act of generating a 3-dimensional representation of a centre-line of a region of interest comprises a modeling approach based on two or more acquired projection images.

4. The method according to claim 1, wherein
the act of generating a 3-dimensional representation of a centre-line of a region of interest comprises a modeling approach based on pre-acquired images data sets of different modalities.

5. The method according to claim 4, wherein
the different modalities are chosen from the group comprising of computer tomogram and magnetic resonance data.

6. A method for determining an optimal trajectory for rotational X-ray angiography for vessel like structures with a C-arm X-ray system,
wherein a C-arm of the C-arm X-ray system has at least two degrees of freedom defined by
a rotational, propeller-type movement of the C-arm expressed in a right or left coronary artery oblique angle $\alpha$, and
a roll motion of the C-arm expressed in a caudal or cranial angle $\beta$, the method comprising the acts of:
generating by a processor a 3-dimensional representation of a centre-line of a body vessel in a region of interest;
generating an optimal view map;
displaying the optimal view map on a display; and
calculating the optimal trajectory, wherein the optimal trajectory is at least defined by movements of the C-arm within its at least two degrees of freedom,
wherein the act of generating a 3D representation of a centre-line of an area of interest comprises a modeling approach based on pre-acquired 3-dimensional rotational angiography images based on non-optimal acquisition trajectories.

7. The method according to claim 6, wherein the act of generating a 3D representation of a centre-line of an area of interest comprises a modeling approach based on a phantom model representing an average of human coronaries.

8. The method according to claim 7, wherein the phantom model is chosen from a group of phantom models comprising a Dudge model.

9. An X-ray C-arm system comprising:
a C-arm with at least two degrees of freedom defined by a rotational propeller-type movement of the C-arm expressed in a left or right coronary artery oblique angle $\alpha$, and
a roll motion of the C-arm expressed in a caudal or cranial angle $\beta$; at least one motor for movements of the C-arm within its at least two degrees of freedom; and
a control unit for controlling the at least one motor so that the movement of the C-arm represents an optimal trajectory;
wherein the control unit is configured to determine the optimal trajectory by performing the acts of:
generating 3-dimensional representation of a centre-line of a body vessel in a region of interest;
generating an optimal view map including a first area including foreshortening and overlapping image projection and a second area including less foreshortening and overlapping of the image projection than the first area;
calculating the optimal trajectory for movements of the C-arm allowing image projections with minimal foreshortening and/or overlap while minimizing an exposure of a region of interest to X-ray; and
automatically manipulating an angle movement of the C-arm based on the generated optimal view map in a way that more of the second area is crossed than the first area,
wherein the act of generating a 3D representation of a centre-line of an area of interest comprises a modeling approach based on pre-acquired 3-dimensional rotational angiography images based on non-optimal acquisition trajectories.

10. An X-ray C-arm system comprising:
a C-arm with at least two degrees of freedom defined by a rotational propeller-type movement of the C-arm expressed in a left or right coronary artery oblique angle $\alpha$, and
a roll motion of the C-arm expressed in a caudal or cranial angle $\beta$; at least one motor for movements of the C-arm within its at least two degrees of freedom; and
a control unit for controlling the at least one motor so that the movement of the C-arm represents an optimal trajectory;
wherein the control unit is configured to determine the optimal trajectory by performing the acts of:
generating 3-dimensional representation of a centre-line of a body vessel in a region of interest;
generating an optimal view map including a first area including foreshortening and overlapping image projection and a second area including less foreshortening and overlapping of the image projection than the first area;
calculating the optimal trajectory for movements of the C-arm allowing image projections with minimal foreshortening and/or overlap while minimizing an exposure of a region of interest to X-ray; and
automatically manipulating an angle movement of the C-arm based on the generated optimal view map in a way that more of the second area is crossed than the first area,
wherein the act of calculating an optimal trajectory comprises the acts of minimizing the following equation:

$$F(\kappa, \lambda, \alpha, \beta) = \sum_{\alpha=-120}^{\alpha=120} \sum_{\beta=-60}^{\beta=60} \kappa f(\alpha, \beta) + \lambda O(\alpha, \beta)$$

wherein:
$\kappa$ is a weighting parameter;
$\lambda$ is a weighting parameter;
$\alpha$ is an angle value of the left or right coronary artery oblique angle;
$\beta$ is an angle value of the caudal or cranial angle;
$f(\alpha, \beta)$ is a function associated with a vessel foreshortening; and
$O(\alpha, \beta)$ is a function associated with a vessel overlap.

11. A computer system for determining an optimal trajectory for 3-dimensional rotational X-ray coronary angiography for a C-arm X-ray system, wherein a C-arm of the C-arm X-ray system has at least two degrees of freedom defined by
   a rotational propeller-type movement of the C-arm expressed in a left or right coronary artery oblique angle $\alpha$, and
   a roll motion of the C-arm expressed in a caudal or cranial angle $\beta$,
   wherein the computer system is adapted to determine the optimal trajectory of the C-arm by performing the acts of:
   generating a 3-dimensional representation of a centre-line of a body vessel in a region of interest;
   generating an optimal view map including a first area including foreshortening and overlapping image projection and a second area including less foreshortening and overlapping of the image projection than the first area;
   calculating the optimal trajectory for the C-arm allowing image projections with minimal foreshortening and/or overlap while minimizing an exposure of an area of interest to X-ray; and
   automatically manipulating an angle movement of the C-arm based on the generated optimal view map in a way that more of the second area is crossed than the first area,
   wherein the act of generating a 3D representation of a centre-line of an area of interest comprises a modeling approach based on pre-acquired 3-dimensional rotational angiography images based on non-optimal acquisition trajectories.

12. A computer system for determining an optimal trajectory for 3-dimensional rotational X-ray coronary angiography for a C-arm X-ray system, wherein a C-arm of the C-arm X-ray system has at least two degrees of freedom defined by
   a rotational propeller-type movement of the C-arm expressed in a left or right coronary artery oblique angle $\alpha$, and
   a roll motion of the C-arm expressed in a caudal or cranial angle $\beta$,
   wherein the computer system, is adapted to determine the optimal trajectory of the C-arm by performing the acts of:
   generating a 3-dimensional representation of a centre-line of a body vessel in a region of interest;
   generating an optimal view map including a first area including foreshortening and overlapping image projection and a second area including less foreshortening and overlapping of the image projection than the first area;
   calculating the optimal trajectory for the C-arm allowing image projections with minimal foreshortening and/or overlap while minimizing an exposure of an area of interest to X-ray; and
   automatically manipulating an angle movement of the C-arm based on the generated optimal view map in a way that more of the second area is crossed than the first area,
   wherein the act of calculating an optimal trajectory comprises the acts of minimizing the following equation:

$$F(\kappa, \lambda, \alpha, \beta) = \sum_{\alpha=-120}^{\alpha=120} \sum_{\beta=-60}^{\beta=60} \kappa f(\alpha, \beta) + \lambda O(\alpha, \beta)$$

wherein:
$\kappa$ is a weighting parameter;
$\lambda$ is a weighting parameter;
$\alpha$ is an angle value of the left or right coronary artery oblique angle;
$\beta$ is an angle value of the caudal or cranial angle;
$f(\alpha, \beta)$ is a function associated with a vessel foreshortening; and
$O(\alpha, \beta)$ is a function associated with a vessel overlap.

13. A non-transitory computer readable medium embodying computer instructions for determining an optimal trajectory for 3-dimensional rotational X-ray coronary angiography for a C-arm X-ray system,
   wherein a C-arm of the C-arm X-ray system has at least two degrees of freedom defined by
   a rotational propeller-type movement of the C-arm expressed in a left or right coronary artery oblique angle $\alpha$, and
   a roll motion of the C-arm expressed in a caudal or cranial angle $\beta$, wherein the computer instructions, when executed by the computer system cause the computer system to perform the following acts to determine the optimal trajectory of the C-arm:
   generating a 3-dimensional representation of a centre-line of a body vessel in a region of interest;
   generating an optimal view map including first, area including foreshortening and overlapping image projection and a second area including less foreshortening and overlapping of the image projection than the first area;
   calculating the optimal trajectory of the C-arm allowing image projections with minimal foreshortening and/or overlap while minimizing an exposure of an areas of interest to X-ray; and
   automatically manipulating an angle movement of the C-arm based on the generated optimal view map in a way that more of the second area is crossed than the first area,
   wherein the act of generating a 3D representation of a centre-line of an area of interest comprises a modeling approach based on pre-acquired 3-dimensional rotational angiography images based on non-optimal acquisition trajectories.

14. A non-transitory computer readable medium embodying computer instructions for determining an optimal trajectory for 3-dimensional rotational X-ray coronary angiography for a C-arm X-ray system,
   wherein a C-arm of the C-arm X-ray system has at least two degrees of freedom defined by
   a rotational propeller-type movement of the C-arm expressed in a left or right coronary artery oblique angle $\alpha$, and
   a roll motion of the C-arm expressed in a caudal or cranial angle $\beta$, wherein the computer instructions, when executed by the computer system cause the computer system to perform the following acts to determine the optimal trajectory of the C-arm:
generating a 3-dimensional representation of a centre-line of a body vessel in a region of interest;
generating an optimal view map including a first area including foreshortening and overlapping image projection and a second area including less foreshortening and overlapping of the image projection than the first area;
calculating the optimal trajectory of the C-arm allowing image projections with minimal foreshortening and/or overlap while minimizing an exposure of an areas of interest to X-ray; and
automatically manipulating an angle movement of the C-arm based on the generated optimal view map in a way that more of the second area is crossed than the first area,
wherein the act of calculating an optimal trajectory comprises the acts of minimizing the following equation:

$$F(\kappa, \lambda, \alpha, \beta) = \sum_{\alpha=-120}^{\alpha=120} \sum_{\beta=-60}^{\beta=60} \kappa f(\alpha, \beta) + \lambda O(\alpha, \beta)$$

wherein:

$\kappa$ is a weighting parameter;

$\lambda$ is a weighting parameter;

$\alpha$ is an angle value of the left or right coronary artery oblique angle;

$\beta$ is an angle value of the caudal or cranial angle;

$f(\alpha, \beta)$ is a function associated with a vessel foreshortening; and $O(\alpha, \beta)$ is a function associated with a vessel overlap.

* * * * *